(12) United States Patent
Würtz et al.

(10) Patent No.: US 7,615,232 B2
(45) Date of Patent: *Nov. 10, 2009

(54) SURFACTANT/SOLVENT SYSTEMS

(75) Inventors: Jochen Würtz, Bingen am Rhein (DE); Gerhard Schnabel, Elsenfeld (DE); Gerhard Frisch, Wehrheim (DE)

(73) Assignee: Bayer CropScience AG, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/975,660

(22) Filed: Oct. 28, 2004

(65) Prior Publication Data

US 2005/0085392 A1    Apr. 21, 2005

Related U.S. Application Data

(60) Continuation of application No. 10/601,019, filed on Jun. 20, 2003, now abandoned, which is a division of application No. 09/746,513, filed on Dec. 21, 2000, now Pat. No. 6,627,595.

(30) Foreign Application Priority Data

Dec. 28, 1999    (DE)    ............... 199 63 381

(51) Int. Cl.
*A01N 25/00* (2006.01)
*C11D 1/00* (2006.01)
*C11D 3/26* (2006.01)
*C11D 3/36* (2006.01)
*C11D 3/43* (2006.01)

(52) U.S. Cl. ............ 424/405; 510/421; 510/436; 510/467; 510/493; 510/499; 510/500; 510/501; 510/502; 510/505; 510/506

(58) Field of Classification Search ........... 510/421, 510/422, 435, 436, 499, 467, 500, 501, 502, 510/505, 506; 424/405
See application file for complete search history.

(56) References Cited

U.S. PATENT DOCUMENTS

| 4,443,362 | A | * | 4/1984 | Guth et al. ............... 510/467 |
|---|---|---|---|---|
| 5,013,747 | A | | 5/1991 | Katayama et al. |
| 5,074,905 | A | | 12/1991 | Frisch et al. |
| 5,259,963 | A | * | 11/1993 | Wiedemann ............... 510/321 |
| 5,650,402 | A | * | 7/1997 | Fost et al. ............... 514/77 |
| 5,674,517 | A | * | 10/1997 | Carpenter ............... 424/405 |
| 5,869,423 | A | | 2/1999 | Frisch et al. |
| 6,627,595 | B2 | * | 9/2003 | Wurtz et al. ............... 510/422 |

FOREIGN PATENT DOCUMENTS

| BX | 597 284 | 5/1961 |
|---|---|---|
| DE | 29 14 164 | 10/1979 |
| EP | 0 328 217 | 8/1989 |
| EP | 0 514 769 | 11/1992 |
| FR | 2 590 119 | 5/1987 |
| FR | 2 597 720 | 10/1987 |
| FR | 2 599 593 | 12/1987 |
| FR | 2599593 | * 12/1987 |
| GB | 2 022 070 | 12/1979 |
| WO | WO 85/01286 | 3/1985 |
| WO | WO 92/09195 | 6/1992 |
| WO | WO 92/09197 | 6/1992 |
| WO | WO 95/23505 | 8/1995 |
| WO | WO 00/56146 | 9/2000 |

* cited by examiner

*Primary Examiner*—Gregory R Del Cotto
(74) *Attorney, Agent, or Firm*—Frommer Lawrence & Haug LLP

(57) ABSTRACT

The present invention relates to surfactant/solvent systems for liquid formulations comprising α) one or more nonaromatic-based surfactants, β) as solvent, one or more triester(s) of phosphoric acid with alcohols, preferably from the group consisting of
1) monohydric alkanols having 5 to 22 carbon atoms, for example with n-, i- or neo-pentanol, n-hexanol, n-octanol, 2-ethylhexanol,
2) diols or polyols, such as ethylene glycol, propylene glycol or glycerol,
3) aryl, alkylaryl, poly(alkyl)aryl and poly(arylalkyl)aryl alcohols, for example with phenol and/or cresol, octylphenol, nonylphenol, triisobutylphenol, tristyrylphenol,
4) alkoxylated alcohols obtained by reacting the alcohols mentioned above under 1), 2) or 3) with alkylene oxides, preferably ($C_1$-$C_4$)alkylene oxides, and
5) alkoxylated alcohols obtained by reacting monohydric alkanols having 1 to 4 carbon atoms and alkylene oxides.

The surfactant/solvent system according to the invention is suitable for the preparation of liquid active substance formulations.

21 Claims, No Drawings

SURFACTANT/SOLVENT SYSTEMS

RELATED APPLICATION

This application is a continuation of application U.S. Ser. No. 10/601,019, filed Jun. 20, 2003 now abandoned, herein incorporated by reference, which in turn is a divisional of application U.S. Ser. No. 09/746,513 filed Dec. 21, 2000, now U.S. Pat. No. 6,627,595 herein incorporated by reference, which in turn claims priority under 35 USC §119 to German application 19963381.9-41, filed Dec. 28, 1999.

The invention relates to the field of combinations of surfactants and solvents. (surfactant/solvent systems) for liquid formulations of active substances (also referred to as liquid preparations), in particular of agrochemical active substances. The invention preferably relates to surfactant/solvent systems for one-phase formulations of one or more agrochemical active substances, where at least one of the active substances, preferably each active substance, is not readily soluble in water. In particular, the invention relates to emulsifiable concentrates (EC) which are based on organic solvents and agrochemical active substances of different polarity. Formulations in the form of oil-based emulsions or suspension concentrates are also possible, and preference is given specifically to emulsifiable concentrates which may comprise one or more agrochemical active substances from the group of the herbicides, insecticides, fungicides, acaricides, molluskicides, rodenticides and/or timber preservatives. Preferred in this context are, inter alia, beet herbicides such as desmedipham, phenmedipham, ethofumesate, metamitron and-herbicides which are of a similar type with regard to their physical and application properties, for example herbicides from the series of the phenoxyphenoxypropionates or of the heteroaryloxyphenoxypropionates.

In general, active substances are employed not as pure materials, but, depending on the field of application and the desired physical composition of the use form, in combination with certain adjuvants, i.e. they are "formulated". Frequently, such formulations contain combinations of various active substances instead of individual active substances to make use, upon application, of the joint properties of the individual active substances, or else because individual active substances are synergistic in combination, i.e. their action is enhanced in a superadditive fashion.

Independently of the type of formulation and of whether the formulations comprise one or more active substances, the aim in particular in the agricultural sector is to achieve the highest possible active substance concentration ("load") of the formulation in question, since a high concentration of the active substances permits the application volumes to be reduced, which, as a consequence, saves material with regard to the adjuvants applied and saves costs in the packaging and transport sector.

Highly concentrated stable formulations and coformulations with environmentally friendly adjuvants are therefore interesting as a matter of principle.

In principle, active substances can be formulated in various ways, depending on the biological and/or chemico-physical parameters specified. In general, examples of suitable formulations which are possible are Wettable powders (WP), oil-in-water (O/W) or water-in-oil (W/O) emulsions, suspensions (SC), suspoemulsions (SE), emulsifiable concentrates (EC), or else granules for soil application or spreading, or water-dispersible granules (WG). The abovementioned formulation types are known in principle and are described, for example, in: Winnacker-Küchler, "Chemische Technologie" [Chemical Engineering], Volume 7, C.Hauser-Verlag, Munich, 4$^{th}$ Edition 1986; van Valkenburg, "Pesticide Formulations", Marcel-Dekker N.Y., 1973; K.Martens, "Spray Drying Handbook", 3rd Ed., 1979, G.Goodwin Ltd. London.

Liquid formulations of herbicides are already known. Thus, for example, WO-A-85/01286 describes liquid formulations which comprise phenmedipham and/or metamitron. Solvents which are mentioned in this context are esters of polyalcohols, ethers, ketones, water-insoluble alcohols, (poly)glycols and oils of vegetable, but also of mineral, origin, and suitable emulsifiers mentioned only in general for the above-described liquid formulations are nonionic, but also ampholytic, cationic or anionic surfactants.

Suitable alternatives to solvent-based emulsifiable concentrates for the abovementioned active substances are inter alia water-containing suspension concentrates (SC) or suspoemulsions (SE). Such formulations are described, for example, in EP-A 0514769, WO-A-95/23505, EP-A-0637910 and WO-A-92/09195.

FR-A-2597720, FR-A-2599593 and FR-A-2590119 describe emulsifiable concentrates which—in deviation from the publications cited above—together with (at least) one herbicide of the biscarbamate type (in particular phenmedipham or desmedipham) comprise a solvent combination of tributyl phosphate and a solvent which is miscible with water, such as, in particular, N-methylpyrrolidone (NMP).

Furthermore, EP-A-0328217 describes emulsifiable concentrates which comprise ethofumesate and, as solvent, tributyl phosphate. The disadvantage in the last-mentioned type of formulation is the use of tributyl phosphate because it is considered to be a dangerous chemical (cf., for example, Chemikaliengesetz [German Chemicals Act]). While this does not make impossible, or ban, the use of tributyl phosphate, the use entails, as a rule, conditions or is generally problematic.

Furthermore, it is known that the biological activity of some pesticidal active substances can be enhanced in some cases by low-molecular weight organic compounds. Thus, in accordance with BE-A-597284, esters or partial esters based on orthophosphoric acid and alkyl-, aryl-, alkylaryl-, cycloalkylaryl- and/or heterocycle-based alcohols are suitable for increasing the action of herbicides, for example herbicidal phenylurea derivatives such as monuron, azoles such as amitrol, triazines such as simazine and propionic acid derivatives such as dalapon. The phosphoric esters specifically described in this context as adjuvants only ericompass phosphoric esters which are relatively unpolar or fully soluble in water and which are not suitable for the preparation of emulsifiable concentrates.

DE-A-2914164 describes synergistic effects which are found in the case of herbicides with a desiccant action on crop plants, i.e. for example herbicides from the group of the phenylureas (for example metoxuron, diuron) or triazines (for example atrazine, simazine), when they are combined with phosphorus-based compositions as are employed in industrial metallurgy for obtaining metals or as plasticizers for polymers. It can be seen unambiguously from the publication that these phosphorus-based compositions, which can be employed for example in industrial metallurgy for obtaining metals or as plasticizers in polymers, are employed as active substances in this context and not as solvents. In other words, this means that the phosphoric acid derivatives in this publication are active substances and not solvents or carriers for agrochemical active substances in the traditional sense. It can also be found in the Japanese Patent Specification JA 29878/69, that, for example, tributoxyethyl phosphate (TBEP) is described as active substance, but not as solvent.

Surprisingly, it has now been found that certain surfactant/solvent systems are suitable in a particular manner for use in the preparation of liquid formulations such as oil dispersions, suspoemulsions, W/O- or O/W-based emulsions and, in particular, of emulsifiable concentrates and corresponding aqueous spray mixtures derived therefrom.

The present invention therefore relates to surfactant/solvent systems for liquid formulations (preparations), comprising α) one or more nonaromatic-based surfactants,
β) as solvent, one or more triester(s) of phosphoric acid with alcohols, preferably from the group consisting of
  1) monohydric alkanols having 5 to 22 carbon atoms, for example n-, i- or neo-pentanol, n-hexanol, n-octanol, 2-ethylhexanol,
  2) diols or polyols, such as ethylene glycol, propylene glycol or glycerol,
  3) aryl, alkylaryl, poly(alkyl)aryl and poly(arylalkyl)aryl alcohols, for example phenol and/or cresol, octylphenol, nonylphenol, triisobutylphenol, tristyrylphenol,
  4) alkoxylated alcohols obtained by reacting the alcohols mentioned above under 1), 2) or 3) with alkylene oxides, preferably ($C_1$-$C_4$)alkylene oxides, and
  5) alkoxylated alcohols obtained by reacting monohydric alkanols having 1 to 4 carbon atoms and alkylene oxides, preferably ($C_1$-$C_4$)alkylene oxides,
  the triester(s) being insoluble in water or soluble in water in a concentration of up to 10 g/l, preferably up to 5 g/l, in particular up to 2 g/l, (=surfactant/solvent system according to the invention).

Subject matter of the invention are also liquid active substance formulations, in particular liquid agrochemical, for example liquid herbicidal, active substance formulations, comprising
(a) one or more active substances, in particular agrochemical, for example herbicidal, active substances, which are insoluble in water or soluble in water up to a concentration of 10 g/l,
(b) the surfactant/solvent system according to the invention (=component mixture (b)),
(c) if appropriate other organic solvents and
(d) if appropriate customary adjuvants and additives such as further surfactants, polymers, fertilizers, odorants, evaporation inhibitors, thickeners, colorants, antifreeze agents and/or preservatives, and
(e) if appropriate water.

Nonaromatic-based surfactants α) which are present in the surfactant/solvent systems according to the invention, are for example heterocycle-, olefin-, aliphatic- or cycloaliphatic-based surfactants α), such as, surface-active pyridine, pyrimidine, triazine, pyrrole, pyrrolidine, furan, thiophene, benzoxazole, benzothiazole and triazole compounds which are substituted by one or more alkyl groups and are subsequently derivatized, e.g. alkoxylated, and which are soluble in the solvent phase are suitable for emulsifying the latter—together with active substances dissolved therein—upon dilution with water (to give a spray mixture).

Examples of such surfactants α) are listed hereinbelow, EO standing for ethylene oxide units, PO for propylene oxide units and BO for butylene oxide units:

α.1) fatty alcohols having 10-24 carbon atoms with 0-60 EO and/or 0-20 PO and/or 0-15 BO in any sequence. The terminal hydroxyl groups of these compounds can be end group-capped by an alkyl, cycloalkyl or acyl radical having 1-24 carbon atoms. Examples of such compounds are: Genapol® C,L,O,T,UD,UDD,X brands from Clariant, Plurafac® and Lutensol®A,AT,ON,TO brands from BASF, Madipal®24 and O13 brands from Condea, Dehypon® brands from Henkel, Ethylan® brands from Akzo-Nobel such as Ethylan CD 120.

α.2) Anionic derivatives of the products described under α.1) in the form of ether carboxylates, sulfonates, sulfates and phosphates and their inorganic salts (for example alkali metal salts and alkaline earth metal salts) and organic salts (for example amine- or alkanolamine-based) such as Genapol®LRO, Sandopan® brands, Hostapha/Hordaphos® brands from Clariant. Copolymers consisting of EO,PO and/or BO units such as, for example, block copolymers such as the Pluronic® brands from BASF and the Synperonic® brands from Uniquema with a molecular weight of 400 to $10^8$. Alkylene oxide adducts of $C_1$-$C_9$ alcohols such as Atlox®5000 from Uniquema or Hoe®-S3510 from Clariant.

Anionic derivatives of the products described under α.3) and α.4) in the form of ether carboxylates, sulfonates, sulfates and phosphates and their inorganic salts (for example alkali metal salts and alkaline earth metal salts) and organic salts (for example amine- or alkanolamine-based).

α.3) Fatty acid and triglyceride alkoxylates such as the Serdo®NOG brands from Condea or the Emulsogen® brands from Clariant, salts of aliphatic, cycloaliphatic and olefinic carboxylic acids and polycarboxylic acids, and alpha-sulfo-fatty acid esters such as those available from Henkel.

α.4) Fatty amide alkoxylates such as the Comperlan® brands from Henkel or the Amam® brands from Rhodia.

Alkylene oxide adducts of alkylnediols such as the Surfynol® brands from Air Products. Sugar derivatives such as aminosugars and amidosugars from Clariant, glucitols from Clariant, alkyl polyglycosides in the form of the APG® brands from Henkel or such as sorbitan esters in the form of the Span® or Tween® brands from Uniquema or cyclodextrin esters or cyclodextrin ethers from Wacker.

α.5) Surface-active cellulose and algin, pectin and guar derivatives such as the Tylose® brands from Clariant, the Manutex® brands from Kelco and guar derivatives from Cesalpina.

Polyol-based alkylene oxide adducts, such as Polyglykol® brands from Clariant. Surface-active polyglycerides and their derivatives from Clariant.

α.6) Sulfosuccinates, alkanesulfonates, paraffin- and olefin-sulfonates such as Netzer IS®, HoeS1728, Hostapur®OS, Hostapur®SAS from Clariant, Triton®GR7ME and GR5 from Union Carbide, Empimin® brands from Albright and Wilson, Marlon®-PS65 from Condea.

α.7) Sulfosuccinamates such as the Aerosol® brands from Cytec or the Empimin® brands from Albright and. Wilson.

α.8) Alkylene oxide adducts of fatty amines, quaternary ammonium compounds having 8 to 22 carbon atoms ($C_{8-22}$) such as, for example, the Genamin® C,L,O,T brands from Clariant.

α.9) Surface-active, zwitterionic compounds such as taurides, betaines and sulfobetaines in the form of Tegotain® brands from Goldschmidt, Hostapon®T and Arkopon®T brands from Clariant.

α.10) Silicone- or silane-based surface-active compounds such as the Tegopren® brands from Goldschmidt and the SE® brands from Wacker and also the Bevaloid®, Rhodorsil® and Silcolapse® brands from Rhodia (Dow Corning, Reliance, GE, Bayer).

α.11) Perfluorinated or polyfluorinated surface-active compounds such as Fluowet® brands from Clariant, the Bayowet® brands from Bayer, the Zonyl® brands from DuPont and products of this type from Daikin and Asahi Glass.

α.12) Surface-active sulfonamides, for example from Bayer.

α.13) Surface-active polyacrylic and polymethacrylic derivatives such as the Sokalan® brands from BASF.

α.14) Surface-active polyamides such as modified gelatin or derivatized polyaspartic acid from Bayer, and their derivatives.

α.15) Surfactant polyvinyl compounds such as modified PVP, such as the Luviskol® brands from BASF and the Agrimer® brands from ISP or the derivatized polyvinyl acetates such as the Mowilith® brands from Clariant or the polyvinyl butyrates such as the Lutonal® brands from BASF, the Vinnapas® and the Ploloform® brands from Wacker or modified polyvinyl alcohols such as the Mowiol® brands from Clariant.

α.16) Surface-active polymers based on maleic anhydride and/or reaction products of maleic anhydride, and copolymers comprising maleic anhydride and/or reaction products of maleic anhydride, such as Agrimer®-VEMA brands from ISP.

α.17) Surface-active derivatives of montan, polyethylene and polypropylene waxes such as the Hoechst® waxes or the Licowet® brands from Clariant.

α.18) Surface-active phosphonates and phosphinates such as Fluowe®-PL from Clariant.

α.19) Polyhalogenated or perhalogenated surfactants such as, for example, Emulsogen®-1557 from Clariant.

The solvent component [component (β)] of the surfactant/solvent system according to the invention are fully reacted, unhydrolyzed esters, i.e. triesters, of phosphoric acid, preferably ortho-phosphoric acid with alcohols, which are insoluble in water or soluble in water up to a concentration of not more than 10 μl. Compounds which are preferably suitable as component (β) are those having alkylene oxide units, for example $C_1$-$C_4$-alkylene oxide units, in particular tri(butoxyethyl) phosphate (TBEP). ($C_1$-$C_4$)alkylene oxide units, for example ethylenoxy, propyleneoxy and/or butyleneoxy units, in particular propyleneoxy and/or ethyleneoxy units, are preferred for alkyleneoxide-units. They are preferable located in the alcohol component of the phosphoric acid ester. Preferred components (β) exhibit 1 to 4 alkylene oxide units, preferably 1 to 4 ($C_1$-$C_4$)alkylene oxide units per unit of alcohol. The molecular weight of the component (β) is preferably smaller than 1000. The compounds of component (β) preferably share the feature that they do not form micellar aggregates in aqueous solutions, for example micellar aggregates which can be detected by light scattering measurements or other methods. This in addition distinguishes them from phosphoric ester surfactants.

Suitable components (β) are the esters of phosphoric acid, e.g. orthophosphoric acid which has been formally reacted three times with alcohols, and the oxalkylates of phosphoric acid, e.g. orthophosphoric acid, which has been formally reacted once and/or twice with alcohols. Examples of suitable compounds are tri-esters of phosphoric acid with alcohols from the group consisting of 1) monohydric alkanols having 5 to 22 carbon atoms, for example with n-, i- or neo-pentanol, n-hexanol, n-octanol, 2-ethylhexanol, 2) diols or polyols, such as ethylene glycol, propylene glycol or glycerol, 3) aryl, alkylaryl, poly(alkyl)aryl and poly(arylalkyl)aryl alcohols, for example with phenol and/or cresol, octylphenol, nonylphenol, triisobutylphenol, tristyrylphenol, 4) alkoxylated alcohols obtained by reacting the alcohols mentioned above under 1), 2) or 3) with alkylene oxides, preferably 1 to 4 units of ($C_1$-$C_4$)alkylene oxides, and 5) alkoxylated alcohols obtained by reacting monohydric alkanols having 1 to 4 carbon atoms and alkylene oxides, preferably 1 to 4 units of ($C_1$-$C_4$)alkylene oxides, which esters are substantially insoluble in water.

Preferred phosphoric esters (component β) are, for example, alkoxylated short-chain alcohols having 1-22 carbon atoms in the alkyl radical and 1 to 30, preferably 1 to 4 alkyleneoxide units in the polyalkyleneoxy moiety which have been reacted completely with ortho-phosphoric acid, for example tributoxyethyl phosphate, alkyl alcohols having 5-22 carbon atoms which have been reacted completely with ortho-phosphoric acid, for example Hostaphat CG 120® (Clariant), tri-n-octyl phosphate ("TOF", Bayer), and optionally alkoxylated alcohols having 1-22 carbon atoms in the alkyl radical and phenol derivatives which have been partially reacted with ortho-phosphoric acid, in each case with 0 to 30, preferably 0 to 4 alkyleneoxide units in the polyalkyleneoxide moiety, the remaining OH valencies of the ortho-phosphoric acid subsequently having been alkoxylated, for example the reaction product of mono/dibutoxyethyl phosphate and 2 mol of ethylene oxide or 2 mol of propylene oxide.

Surprisingly, the surfactant/solvent system according to the invention allows stable active substance formulations to be prepared, for example formulations of active substances, in particular agrochemical, for example herbicidal, active substances which are insoluble in water or soluble in water up to a concentration of 10 g/l. Examples of such active substance formulations are visually transparent and thermodynamically stable emulsifiable concentrates, thermodynamically unstable O/W and W/O emulsions, suspoemulsions or suspension concentrates, inter alia of agrochemical, preferably herbicidal, active substances such as biscarbamate herbicides (for example desmedipham and/or phenmedipham), and/or sulfonate herbicides (for example ethofumesate) and/or triazinone herbicides (for example metamitron). In addition, the surfactant system according to the invention may have a favorable effect on the pesticidal action of the agrochemical active substance(s) incorporated.

Also, the surfactant/solvent system according to the invention permits the preparation of formulations with active substances other than those mentioned above as long as they have similar properties with regard to their solubility. For example, others which are suitable are herbicides from the group of the phenoxyphenoxypropionates such as diclofop-methyl, of the heteroaryloxyphenoxy-propionates such as fenoxaprop-ethyl or clodinafop-propargyl, of the triazinones, such as metamitron, of the sulfonylureas, such as triflusulfuron-methyl, or other active substances such as prochloraz and/or insecticides such as deltamethrin. This shows the flexibility of the surfactant/solvent system described. The compounds mentioned are known to the skilled worker for example from "The Pesticide Manual", British Crop Protection Council, 11th edition, 1997.

Other organic solvents (c) which are suitable are, for example, unpolar solvents, polar protic or aprotic dipolar solvents and their mixtures. Examples of other organic solvents for the purposes of the invention are aliphatic or aromatic hydrocarbons such as, for example, mineral oils, paraffins or toluene, xylenes and naphthalene derivatives, in particular 1-methylnaphthalene, 2-methylnaphthalene, mixtures of $C_6$-$C_{16}$-aromatics such as, for example, the Solvesso® series (ESSO) with the types Solvesso® 100 (b.p. 162-177° C.), Solvesso® 150 (b.p. 187-207° C.) and Solvesso® 200 (b.p. 219-282° C.) and 6-20C aliphatics which can be linear or cyclic, such as the products of the Shellsol® series, types T and K, or BP-n paraffins, halogenated aliphatic or aromatic hydrocarbons such as methylene chloride or chlorobenzene, mono- and/or polybasic esters such as, for example, triacetin (acetic acid triglyceride), butyrolactone, propylene carbonate, triethyl citrate and ($C_1$-$C_{22}$)alkyl phthalates, specifically ($C_4$-$C_8$)alkyl phthalates, ethers such as diethyl ether, tetrahydrofuran (THF), dioxane, alkylene glycol monoalkyl ethers and alkylene glycol dialkyl ethers such as, for example, propylene glycol monomethyl ether, specifically Dowanol® PM (propylene glycol monomethyl ether), propylene glycol monoethyl ether, ethylene glycol monomethyl ether or ethylene glycol monoethyl ether, diglyme and tetraglyme, amides such as dimethylformamide (DMF), dimethylacetamide, dimethylcaprylic/capric amide and N-alkylpyrrolidones, ketones such as acetone, which is water-soluble, but also ketones which are not miscible with water, such as, for example, cyclohexanone or isophorone, nitriles such as acetonitrile, propionitrile, butyronitrile and benzonitrile, sulfoxides and sulfones such as dimethyl sulfoxide (DMSO) and sulfolane, and oils in general, for example vegetable oils such as corn oil and rapeseed oil.

Further preferred organic solvents for the purposes of the present invention are, in particular, amides such as dimethylcaprylic/capric amide and N-methylpyrrolidone, or aromatic solvents such as the Solvesso® series from Exxon.

The adjuvants and additives used for the preparation of the above-mentioned formulations, such as, in particular, surfactants and solvents, are known in principle, and are described, for example, in standard works: McCutcheon's "Detergents and Emulsifiers Annual", MC Publ. Corp., Ridgewood N.J.; Sisley and Wood, "Encyclopedia of Surface active Agents", Chem. Publ.Co.Inc., N.Y. 1964; Schönfeldt, "Grenzflächenaktive Äthylenoxidaddukte" [Surface-active ethylene oxide adducts], Wiss. Verlagsgesellschaft, Stuttgart 1976; Winnacker-Küchler, "Chemische Technologie" [Chemical Engineeering], Volume 7, C.Hauser-Verlag, Munich, $4^{th}$ edition, 1986.

While the chemical structure of the individual components which can be employed is described in sufficient detail in the abovementioned standard works, predictions regarding the properties of mixtures of such components for formulating an active substance cannot be deduced from the abovementioned standard works.

Surprisingly, it has now been found that combinations of an in water insoluble or up to 10 g/l in water soluble phosphoric-acid tri-ester as solvent and one or more nonaromatic-based surfactants are particularly well suited for the preparation of liquid formulations of active substances such as stable emulsifiable concentrates, emulsions, suspoemulsions or suspension concentrates, which are also an object of the present invention.

The liquid formulations according to the invention can be prepared by the customary processes which are already known, for example by mixing the various components with the aid of stirring, shaking or (static) mixers. If appropriate, it is advantageous to briefly heat the samples in order to ensure the complete dissolution of all the components involved.

One factor for the selection of preferred surfactant components is their acidity or basicity per unit weight or volume, which is expressed, for example, by the acid number or amine number. When selecting further surfactant components, it is advantageous to ensure that the total acid number or amine number does not increase unduly. Preferably suitable, besides nonionic surfactants, are therefore for example acidic or basic surfactant components with sufficiently small acid or amine numbers, or nonionic surfactant components. Accordingly, additional nonionic surfactant components which can be employed are, for example, castor oil which has been reacted with 40 mol of EO or else castor oil which has been reacted with 12 mol of EO, oleic acid which has been reacted with 15 mol of EO, and EO/PO/EO block copolymers.

In this connection it must furthermore be mentioned that the surfactant/solvent systems of the present invention allow the preparation of stable formulations with an active substance load and active substance composition which can be varied within Wide limits. Thus, the active substance load may vary for instance between 20 and 40, preferably between 24 and 30, percent by weight. As regards the active substance composition, not only stable formulations with one active substance, but also formulations with two or, in particular, three active substances, can be obtained using this component mixture.

The above-described surfactant/solvent systems are preferably suitable for the preparation of formulations with herbicidal active substances such as diclofop-methyl, fenoxaprop-ethyl, prochloraz, metamitron and/or deltamethrin.

Preferred ratios of the components phosphoric ester (β): surfactant (α) are, in particular, 100:1 to 1:100, especially preferably 1:5 to 1:20, for example approximately 1:8, 1:9 or 1:10, or 1:0., 25 to 1:0., 9, for example 1.3:1, 1.4:1 or 1.5:1, depending on the active substance load and the active substance composition of the formulations.

The surfactant/solvent system according to the invention permits the preparation of various liquid formulations, such as oil dispersions, suspoemulsions, W/O- or O/W-based emulsions and, in particular, of emulsifiable concentrates and corresponding liquid formulations derived therefrom, such as aqueous spray mixtures.

Emulsifiable concentrates which are prepared in accordance with the present invention comprise a priori no added water, but only the residual water present in the abovementioned commercially available surfactants and surfactant mixtures, polymers and solvents. Owing to the surfactants present in the emulsfiable concentrates of the present invention, however, it is possible for these to be diluted with water as far as a critical volume fraction without this leading to cloudiness or the formulation becoming unstable. Formally, this first gives rise to W/O microemulsions which, upon further increasing the water fraction, become W/O emulsions and finally—upon further dilution with water—O/W emulsions. The invention therefore also encompasses liquid formulations which, besides the surfactant/solvent mixture b) according to the invention, comprise (added) water, for example microemulsions.

The component mixtures (b) allow preferably liquid preparations of active substances, in particular herbicidal active substances such as desmedipham and/or phenmedipham and/or ethofumesate, to be prepared, which comprise
a) 1 to 50% by weight, preferably 15 to 35% by weight, of agrochemical active substances,
b) 5 to 80% by weight, preferably 10 to 70% by weight, of the surfactant/solvent system (b) according to the invention,
c) 0 to 40% by weight, preferably 5 to 35% by weight, of further organic solvents,
d) 0 to 20% by weight, preferably 0 to 10% by weight, of customary adjiuvants and additives, such as formulation auxiliaries, and
e) 0 to 96% by weight, preferably 0 to 90% by weight, in particular 0 to 10% by weight, of water.

Examples of customary adjiuvants and additives such as formulation auxiliaries d) are antifreeze agents, evaporation inhibitors, preservatives, odorants and colorants.

Preferred formulation auxiliaries d) are antifreeze agents and evaporation inhibitors such as glycerol, for example in an amount of 2 to 10% by weight, and preservatives, for example Mergal K9N® (Riedel) or Cobate C® in the use concentrations which are customary for the agents employed in each case.

Since anhydrous emulsfiable concentrates constitute an advantageous use form of the active substances, in particular herbicidal active substances of type (a), an especially preferred subject matter of the invention are emulsifiable concentrates which comprise
a) 10 to 40% by weight of active substances of the abovementioned type (a),
b) 10 to 60% by weight of the surfactant/solvent system (b) according to the invention,
c) 5 to 35% by weight of further organic solvents and
d) 0 to 10% by weight of customary adjuvants and additives, for example formulation auxiliaries.

In analogy to anhydrous emulsfiable concentrates, the oil-based suspension concentrates, which are likewise anhydrous, constitute a preferred subject matter of this invention, these preparations comprising
a) 10 to 40% by weight of active substances of the abovementioned type (a),
b) 10 to 60% by weight of the surfactant/solvent system (b) according to the invention,
c) 5 to 35% by weight of further organic solvents,
d) 0 to 10% by weight of customary adjuvants and additives other than (e), such as formulation auxiliaries, and
e) 0.001 to 20% by weight of organic and/or inorganic thickeners.

Furthermore, emulsions may also be prepared with the surfactant/solvent systems according to the invention. A further especially preferred subject matter of the invention are therefore emulsions or microemulsions comprising
a) 10 to 40% by weight of active substances of the abovementioned type (a),
b) 10 to 60% by weight of the surfactant/solvent system (b) according to the invention,
c) 5 to 35% by weight of further organic solvents and
d) 0 to 10% by weight of customary adjuvants and additives, such as formulation auxiliaries and
e) 0.001 to 95% by weight of water.

The suspoemulsions which can be prepared with the above-described surfactant/solvent systems also constitute a preferred subject matter of the invention. These comprise
a) 10 to 40% by weight of active substances of the abovementioned type (a),
b) 10 to 60% by weight of the surfactant/solvent system (b) according to the invention,
c) 5 to 35% by weight of further organic solvents and
d) 0 to 10% by weight of customary adjuvants and additives other than (f), such as formulation auxiliaries and
e) 0.001 to 95% by weight of water and
f0 0.001 to 20% by weight of organic and/or inorganic thickeners.

Upon dilution with water, the surfactant/solvent system according to the invention (component mixture b)) results in dispersions of oil phases in water or, when the appropriate individual components have been chosen, of aqueous phases in oil. Accordingly, dispersions can be obtained which can be diluted either with water or with oil while retaining the colloidal structure, depending on the composition. The dispersions which can be obtained from the above-described concentrates by dilution are therefore another subject matter of the invention.

The surfactant/solvent system according to the invention is suitable for the preparation of stable liquid formulations, in particular emulsifiable concentrates. The formulations and spray mixtures which can be prepared with the surfactant/solvent system according to the invention also give results which are advantageous from the biological angle upon use. An effective amount of the formulation or of the spray mixture, if necessary after dilution with water, is applied to the plants, plant parts or the area on which the plants grow, for example the area under cultivation. Moreover, the biological activity of the agrochemical active substances employed can be increased synergistically by employing the surfactant/solvent component b) according to the invention.

EXAMPLES

In the examples which follow, stated quantities are based on weight unless otherwise specified. The examples of Table 1 refer to comparative examples not in accordance with the invention, while the examples of Table 2 are in accordance with the invention and describe emulsifiable concentrates (Examples I-VII), emulsions (Examples VIII and XI), suspoemulsions (Example IX) and suspension concentrates (Example X). The formulations were prepared by mixing the components with a stirrer.

TABLE 1

Examples of formulations which give no stable emulsifiable concentrates (EC)

|  | 1 | 2 | 3 | 4 |
|---|---|---|---|---|
| Fenoxaprop-p-ethyl |  | 15 |  |  |
| Endosulfan | 40 |  |  |  |
| Deltamethrin |  |  |  | 5 |
| Metamitron |  |  | 1 |  |
| Rapeseed oil | 27 | 40 | 57 | 30 |
| Genapol X-060[4] | 15 | 20 | 20 | 30 |
| Emulsogen EL-400[5] | 14 | 19 | 18 | 25 |
| Phosfetal 201[8] | 4 | 4 | 4 | 10 |
| Servoxyl VPDZ 20/100[7] |  | 2 |  |  |

TABLE 2

Examples of formulations according to the invention which give stable formulations

| | I | II | III | IV | V | VI | VII | VIII | IX | X | XI |
|---|---|---|---|---|---|---|---|---|---|---|---|
| Ethofumesate | 12.5 | | | | | 38.4 | | 10.5 | 13.7 | 15.8 | 10.5 |
| Phenmedipham | 10.0 | | | | | | | 8.5 | 11.1 | 12.8 | 8.5 |
| Desmedipham | 8.0 | | | | | | | 6.5 | 8.5 | 9.8 | 6.5 |
| Diclofop-methyl | | 15.0 | | | | | | | | | |
| Fenoxaprop-p-ethyl | | | 15.0 | | | | | | | | |
| Prochloraz | | | | 40.0 | | | | | | | |
| Deltamethrin | | | | | 5.0 | | | | | | |
| Metamitron | | | | | | | 1.5 | | | | |
| Tributoxyethyl phosphate[1] | 25.5 | 40.0 | 40.0 | 27.0 | 45.0 | 21.6 | 42.5 | 27.5 | 12.6 | 12.0 | 22.5 |
| Rapeseed oil | | | | | | | | | | 9.8 | |
| Genapol X-060[4] | 20.0 | 20.0 | 20.0 | 15.0 | 20.0 | 20.0 | 27.0 | 15.0 | 15.0 | 20.0 | 15.0 |
| Genapol PF 20[6] | | | | | | | | | 10.0 | 9.8 | 14.0 |
| Emulsogen EL 400[5] | 18.0 | 19 | 19.0 | 14.0 | 20.0 | 16.0 | 24.0 | | | | 12.0 |
| Phosfetal 201[8] | 4.0 | 4.0 | 4.0 | 4.0 | 10.0 | 4.0 | 5.0 | | | 5.0 | 3.0 |
| Servoxyl VPDZ 20/100[7] | 2.0 | 2.0 | 2.0 | | | | | | | | |
| HOE S3618[2] | | | | | | | | 2.5 | 2.5 | | 3.0 |
| Bentone 38[3] | | | | | | | | | | 0.8 | |
| Drinking water | | | | | | | | 19.5 | 26.8 | | 19.0 |

Explanations for Tables 1 and 2:
1) Tributoxyethyl phosphate (specifically Hostaphat B310®, Clariant)
2) Neutralized, phosphated ethylene oxide/propylene oxide/ethylene oxide block copolymer (specifically HOE®S3618, Clariant)
3) Silica derivative (specifically Bentone®38)
4) Ethoxylated i-$C_{13}$-fatty alcohol (specifically Genapol X-060®, Clariant)
5) Ethoxylated castor oil (specifically Emulsogen EL 400®, Clariant)
6) Ethylene oxide/propylene oxide/ethylene oxide block copolymer (specifically Genapol PF 20®, Clariant)
7) Phosphated ethoxylated isotridecyl alcohol (specifically Servoxyl VPDZ 20/100®, Condea)
8) Phosphated ethoxylated fatty alcohol (specifically Phosfetal 201®, Zschimmer & Schwarz)

We claim:

1. A liquid active substance formulation in the form of an emulsifiable concentrate, microemulsion, oil-dispersion, suspoemulsion or emulsion which consists of:
   a) one or more agrochemical active substances which are insoluble in water or soluble up to a concentration of 10 g/l,
   b) a surfactant/solvent system of
      α) one or more nonaromatic-based surfactants; and
      β) as a solvent, one or more triester(s) of phosphoric acid formed from phosphoric acid reacted with alcohols, wherein
         the alcohols are selected from the group consisting of
         1) monohydric alkanols having 5 to 22 carbon atoms,
         2) diols or polyols,
         3) aryl, alkylaryl, poly(alkyl)aryl and poly(arylalkyl) aryl alcohols,
         4) alkoxylated alcohols obtained by reacting the alcohols mentioned above under 1), 2) or 3) with alkylene oxides, and
         5) alkoxylated alcohols obtained by reacting monohydric alkanols having 1 to 4 carbon atoms and alkylene oxides;
   c) optionally further organic solvents;
   d) optionally adjuvants and additives selected from the group consisting of, fertilizers, odorants, evaporation inhibitors, thickeners, colorants, antifreeze agents and preservatives; and
   e) optionally water.

2. The liquid active substance formulation of claim 1 wherein for the surfactant/solvent system the triester(s) are insoluble in water or are soluble in water up to a concentration of not more than 10 g/l.

3. The liquid active substance formulation of claim 1 wherein for surfactant/solvent system component β) is at least one compound selected from the group consisting of
   alkoxylated short-chain alcohols having 1-22 carbon atoms in the alkyl radical and 1 to 30 alkyleneoxy units in the polyalkyleneoxy moiety which have been reacted completely with ortho-phosphoric acid,
   alkyl alcohols having 5-22 carbon atoms which have been reacted completely with ortho-phosphoric acid,
   optionally alkoxylated alcohols having 1-22 carbon atoms in the alkyl radical and phenol derivatives, which have been partially reacted with ortho-phosphoric acid, in each case with a 0 to 30 alkyleneoxy units in the polyalkyleneoxy moiety, the remaining OH valencies of the orthophosphoric acid subsequently having been alkoxylated, and esters of n-octylphosphonic acid which has formally been reacted twice with alcohols.

4. The liquid active substance formulation as claimed in claim 1, wherein
   a) 1 to 50% by weight of agrochemical active substances,
   b) 5 to 80% by weight of the surfactant/solvent system,
   c) 0 to 40% by weight of further organic solvents,
   d) 0 to 20% by weight of adjuvants and additives, and
   e) 0 to 94% by weight of water is present.

5. The liquid active substance formulation as claimed in claim 1 which is in the form of an emulsifiable concentrate.

6. The emulsifiable concentrate as claimed in claim 5 wherein
   a) 10 to 40% by weight of agrochemical active substances,
   b) 10 to 60% by weight of the surfactant/solvent system,
   c) 5 to 35% by weight of further organic solvents, and
   d) 0 to 10% by weight of adjuvants and additives is present.

7. The liquid active substance formulation as claimed in claim 1, wherein the one or more agrochemical active substances is selected from the group of the herbicides consisting of desmedipham, phenmedipham, ethofumesate and mixtures thereof.

8. A process for the preparation of the liquid active substance formulation as defined in claim 1, wherein the components a) and b) are mixed with each other and optionally components c), d) and/or e) are also mixed together with components a) and b).

9. A liquid active substance formulation as claimed in claim 1 wherein:
the optionally further organic solvents is selected from the group consisting of:
(a) aliphatic or aromatic hydrocarbons
(b) halogenated aliphatic or aromatic hydrocarbons
(c) mono- and/or polybasic esters
(d) ethers
(e) amides
(f) ketones
(g) nitriles
(h) sulfoxides and sulfones; and
(i) oils.

10. The emulsifiable concentrate of claim 5, wherein the at least one agrochemical active substance is selected from the group of the herbicides consisting of desmedipham, phenmedipham, and ethofumesate and mixtures thereof.

11. The liquid active substance formulation in the form of an emulsifiable concentrate, microemulsion or emulsion of claim 1, wherein:
a) 15 to 35% by weight of agrochemical active substances,
b) 10 to 70% by weight of the surfactant/solvent system,
c) 5 to 35% by weight of further organic solvents,
d) 0 to 10% by weight of adjuvants and additives; and
e) 0 to 90% by weight of water is present.

12. An emulsifiable concentrate as claimed in claim 5, wherein the emusifiable concentrate is an anhydrous emulsifiable concentrate and wherein:
a) 10 to 40% by weight of agrochemical active substances,
b) 10 to 60% by weight of the surfactant/solvent system,
c) 5 to 35% by weight of further organic solvents, and
d) 0 to 10% by weight of adjuvants and additives is present.

13. The liquid active substance formulation in the form of an emulsifiable concentrate, microemulsion or emulsion of claim 1, wherein the ratio of one or more triester(s) of phosphoric acid to one or more nonaromatic-based surfactants is from 100:1 to 1:100.

14. The liquid active substance formulation in the form of an emulsifiable concentrate, microemulsion or emulsion of claim 13 wherein the ratio of one or more triester(s) of phosphoric acid to one or more nonaromatic-based surfactants is from 1:5 to 1:20.

15. The liquid active substance formulation in the form of an emulsifiable concentrate, microemulsion or emulsion of claim 1, wherein the one or more triester(s) of phosphoric acid is insoluble in water or is soluble in water in a concentration up to 5 g/L.

16. The liquid active substance formulation in the form of an emulsifiable concentrate, microemulsion or emulsion of claim 15, wherein the one or more triester(s) of phosphoric acid is insoluble in water or is soluble in water in a concentration up to 2 g/L; the ratio of one or more triester(s) of phosphoric acid to one or more nonaromatic-based surfactants is from 1:5 to 1:20 and the one or more agrochemical active substances selected from the group of the herbicides consisting of desmedipham, phenmedipham, ethofumesate and mixtures thereof.

17. The liquid active substance formulation in the form of an emulsifiable concentrate, microemulsion or emulsion of claim 13 wherein the ratio of one or more triester(s) of phosphoric acid to one or more nonaromatic-based surfactants is from 1:0.25 to 1:0.9.

18. The liquid active substance formulation of claim 1, wherein the optionally further organic solvents is selected from the group consisting of:
(a) mineral oils, paraffins, toluene, xylenes, naphthalene derivatives, 1-methylnaphthalene, 2-methylnaphthalene, $C_6$-$C_{16}$-aromatics and linear or cyclic $C_6$-$C_{20}$ aliphatics,
(b) methylene chloride and chlorobenzene,
(c) acetic acid triglyceride, butyrolactone, propylene carbonate, triethyl citrate and ($C_1$-$C_{22}$)alkyl phthalates, ($C_4$-$C_8$)alkyl phthalates,
(d) diethyl ether, tetrahydrofuran (THF), dioxane, alkylene glycol monoalkyl ethers, alkylene glycol dialkyl ethers, propylene glycol monomethyl ether, propylene glycol monomethyl ether, propylene glycol monoethyl ether, ethylene glycol monomethyl ether, ethylene glycol monoethyl ether, diglyme and tetraglyme,
(e) dimethylformamide (DMF), dimethylacetamide, dimethylcaprylic/capric amide and N-alkylpyrrolidones,
(f) acetone, cyclohexanone and isophorone,
(g) acetonitrile, propionitrile, butyronitrile and benzonitrile,
(h) dimethyl sulfoxide (DMSO) and sulfolane, and
(i) vegetable oils, corn oil and rapeseed oil.

19. The liquid active substance formulation in the form of an emulsifiable concentrate, microemulsion, oil-dispersion, suspoemulsion or emulsion which consists of:
a) one or more agrochemical active substances which are insoluble in water or soluble up to a concentration of 10 g/l; and
b) a surfactant/solvent system of:
α) one or more nonaromatic-based surfactants; and
β) as a solvent, one or more triester(s) of phosphoric acid formed from phosphoric acid reacted with alcohols, wherein
the alcohols are selected from the group consisting of
1) monohydric alkanols having 5 to 22 carbon atoms,
2) diols or polyols,
3) aryl, alkylaryl, poly(alkyl)aryl and poly(arylalkyl) aryl alcohols,
4) alkoxylated alcohols obtained by reacting the alcohols mentioned above under 1), 2) or 3) with alkylene oxides, and
5) alkoxylated alcohols obtained by reacting monohydric alkanols having 1 to 4 carbon atoms and alkylene oxides.

20. The liquid active substance formulation of claim 18, wherein the optionally adjuvants and additives selected from the group consisting of fertilizers, evaporation inhibitors, colorants, and preservatives.

21. The liquid active substance formulation of claim 18, wherein the optionally further organic solvents is selected from the group consisting of rapeseed oil, dimethylcaprylic/capric amide, N-methylpyrrolidone and $C_6$-$C_{16}$ aromatics.

* * * * *